United States Patent
Bhattacharya

(10) Patent No.: US 12,044,556 B2
(45) Date of Patent: Jul. 23, 2024

(54) METHOD AND APPARATUS FOR REAL TIME RESPIRATORY GATING SIGNAL GENERATION AND DETECTION OF BODY DEFORMATION USING EMBEDDED FIBER BRAGG GRATINGS

(71) Applicant: EmpNia Inc., Edina, MN (US)

(72) Inventor: Manojeet Bhattacharya, Edina, MN (US)

(73) Assignee: EmpNia Inc., Edina, MN (US)

( * ) Notice: Subject to any disclaimer, the term of this patent is extended or adjusted under 35 U.S.C. 154(b) by 332 days.

(21) Appl. No.: 17/224,855

(22) Filed: Apr. 7, 2021

(65) Prior Publication Data
US 2021/0223068 A1    Jul. 22, 2021

Related U.S. Application Data

(63) Continuation-in-part of application No. PCT/US2020/065691, filed on Dec. 17, 2020, which
(Continued)

(51) Int. Cl.
*G01D 5/353*    (2006.01)
*A41D 13/12*    (2006.01)
(Continued)

(52) U.S. Cl.
CPC ..... *G01D 5/35316* (2013.01); *A41D 13/1281* (2013.01); *A61B 5/6804* (2013.01);
(Continued)

(58) Field of Classification Search
None
See application file for complete search history.

(56) References Cited

U.S. PATENT DOCUMENTS 7,257,436 B2    8/2007    Sasaki et al.
7,678,063 B2    3/2010    Felmlee et al.
(Continued)

FOREIGN PATENT DOCUMENTS

JP    2014-525764 A    10/2014
JP    2017-506543 A    3/2017
(Continued)

OTHER PUBLICATIONS

Anzai Medical, Co.,Ltd, "Respiratory Gating System AZ-733V1: What is a Respiratory Gating System," http://www.anzai-med.co.jp, no date given.
(Continued)

*Primary Examiner* — Jerry Rahll

(57) ABSTRACT

A method and system of compensating for body deformation during image acquisition or external beam treatment includes acquiring image data of a body and peak wavelength data from a plurality of fiber Bragg gratings (FBGs) disposed on the body aligned along a predetermined coordinate system on the body, such as a cartesian coordinate system. The method further comprises detecting effective shifts of the Bragg wavelengths of the FBGs caused by body deformation during image acquisition, and controlling the movement of the body through a cavity in a scanning device and controlling the acquisition of the image data or external beam treatment during body deformation based on the effective shifts of the Bragg wavelengths of the FBGs.

24 Claims, 10 Drawing Sheets

Related U.S. Application Data is a continuation-in-part of application No. 16/723,352, filed on Dec. 20, 2019, now Pat. No. 11,041,740.

(51) Int. Cl.
    *A61B 5/00* (2006.01)
    *G01L 1/24* (2006.01)
    *G02B 6/02* (2006.01)

(52) U.S. Cl.
    CPC ..... *G01D 5/35335* (2013.01); *G01D 5/35367* (2013.01); *G01L 1/246* (2013.01); *G02B 6/022* (2013.01)

(56) References Cited

U.S. PATENT DOCUMENTS

| | | | |
|---|---|---|---|
| 8,553,959 B2 | 10/2013 | Hsieh et al. | |
| 9,116,055 B2* | 8/2015 | Johnston | G01K 11/3206 |
| 9,304,018 B2* | 4/2016 | Davis | A61B 5/1079 |
| 9,730,654 B2 | 8/2017 | Erbel et al. | |
| 9,841,331 B2* | 12/2017 | Wood | A61B 5/1036 |
| 10,234,934 B2* | 3/2019 | Connor | G06F 3/017 |
| 10,321,873 B2* | 6/2019 | Connor | A61B 5/6831 |
| 10,332,644 B2 | 6/2019 | Garcia | |
| 10,488,916 B2* | 11/2019 | Hahami | A61B 5/6805 |
| 10,524,701 B2* | 1/2020 | Kim | A61B 5/6847 |
| 10,716,510 B2* | 7/2020 | Connor | A61B 5/6804 |
| 11,041,740 B1 | 6/2021 | Bhattacharya | |
| 11,504,010 B2 | 11/2022 | Bhattacharya | |
| 2009/0185772 A1 | 7/2009 | Xia et al. | |
| 2013/0211261 A1 | 8/2013 | Wang et al. | |
| 2014/0064332 A1* | 3/2014 | Johnston | G01K 11/3206 |
| | | | 374/161 |
| 2014/0088377 A1* | 3/2014 | Manzke | A61B 5/1073 |
| | | | 600/595 |
| 2014/0128721 A1* | 5/2014 | Forthmann | A61B 5/055 |
| | | | 600/407 |
| 2014/0238153 A1* | 8/2014 | Wood | A43B 13/203 |
| | | | 73/862.627 |
| 2015/0124266 A1* | 5/2015 | Davis | G01D 5/3538 |
| | | | 356/601 |
| 2015/0359455 A1* | 12/2015 | Hahami | A61B 5/6804 |
| | | | 600/476 |
| 2016/0202755 A1* | 7/2016 | Connor | G06F 3/011 |
| | | | 73/865.4 |
| 2016/0256710 A1 | 9/2016 | Goldstein et al. | |
| 2016/0338644 A1* | 11/2016 | Connor | A61B 5/1126 |
| 2016/0361194 A1* | 12/2016 | Hautvast | A61B 18/24 |
| 2017/0007849 A1* | 1/2017 | Hautvast | A61N 5/1001 |
| 2017/0049341 A1 | 2/2017 | Karabacak et al. | |
| 2017/0354353 A1* | 12/2017 | Kim | G01L 1/246 |
| 2018/0008196 A1* | 1/2018 | Connor | A61B 5/1126 |
| 2018/0364115 A1* | 12/2018 | Brown | G01D 5/35374 |
| 2019/0336038 A1* | 11/2019 | Gorgutsa | A61B 5/0816 |
| 2021/0190549 A1 | 6/2021 | Bhattacharya | |
| 2023/0070912 A1 | 3/2023 | Bhattacharya | |

FOREIGN PATENT DOCUMENTS

| | | |
|---|---|---|
| JP | 2017-506555 A | 3/2017 |
| JP | 2017-519221 A | 7/2017 |
| WO | 2012/168836 A2 | 12/2012 |
| WO | 2015/128179 A1 | 9/2015 |
| WO | 2015/128392 A1 | 9/2015 |
| WO | WO-2015167340 A1 | 11/2015 |
| WO | 2016/147795 A1 | 9/2016 |
| WO | 2019/031041 A1 | 2/2019 |
| WO | 2021/127207 A1 | 6/2021 |
| WO | 2021/127233 A1 | 6/2021 |

OTHER PUBLICATIONS

Liu, Jie et. al., "Evaluation of the combined use of two different respiratory monitoring systems for 4D CT simulation and gated treatment," Journal of Applied Clinical Medical Physics, Wiley 19:5 pp. 666-675, (2018).

Roylance, David, "Stress-Strain Curves, Department of Materials Science and Engineering," Massachusetts Institute of Technology, Cambridge, MA, Aug. 23, 2001.

U.S. Non-Final Office Action for U.S. Appl. No. 16/723,352, entitled "Method And Apparatus For Real Time Respiratory Gating Signal Generation And Detection Of Body Deformation Using Embedded Fiber Bragg Gratings," dated Nov. 24, 2020.

U.S. Notice of Allowance for U.S. Appl. No. 16/723,352, entitled "Method And Apparatus For Real Time Respiratory Gating Signal Generation And Detection Of Body Deformation Using Embedded Fiber Bragg Gratings," dated Jan. 22, 2021.

Lau, Doreen et al. "Intensity-Modulated Microbend Fiber Optic Sensor for Respiratory Monioring and Gating During MRI,"IEEE Transactions on Biomedical Engineering, vol. 60, No. 9, Sep. 2013.

PCT Invitation to Pay Additional Fees for PCT Application No. PCT/US2020/065691, entitled "Method and Apparatus for Real Time Respiratory Gating Signal Generation and Detection of Body Deformation Using Embedded Fiber Bragg Gratings," dated Apr. 9, 2021.

International Search Report and Written Opinion for PCT Application No. PCT/US2020/065691, entitled "Method and Apparatus for Real Time Respiratory Gating Signal Generation and Detection of Body Deformation Using Embedded Fiber Bragg Gratings," dated Jun. 1, 2021.

Office Action for Japanese Application No. JP20220538314 with English translation, dated May 1, 2023, 8 pages.

Office Action for Japanese Application No. JP20220538314 with English translation, dated Nov. 7, 2023, 5 pages.

EP Application No. 20841823.6 Notice to Grant dated Apr. 4, 2024, 12 pages.

* cited by examiner

METHOD AND APPARATUS FOR REAL TIME RESPIRATORY GATING SIGNAL GENERATION AND DETECTION OF BODY DEFORMATION USING EMBEDDED FIBER BRAGG GRATINGS

RELATED APPLICATION(S)

This application is a continuation-in-part of International Patent Application Serial No. PCT/US2020/065691, filed on Dec. 17, 2020, which designates the U.S., published in English, and which is a continuation-in-part of U.S. patent application Ser. No. 16/723,352 (now U.S. Pat. No. 11,041,740), filed Dec. 20, 2019. The entire teachings of the above applications are incorporated herein by reference.

BACKGROUND

Anatomic and functional imaging modalities such as computed tomography (CT), magnetic resonance imaging (MM), and positron and single photon emission tomography (PET and SPECT) suffer from image degradation due to respiratory motion of the patient. And even though in some instances of CT scans the patient is asked to hold their breath during the image acquisition, this is not always feasible as not all patients can hold their breath due to their age and/or physical condition. Additionally, breath hold CT scans are typically higher radiation dose scans as the scan needs to be completed quickly which can only be accomplished by increasing the x-ray flux and moving the table quickly. In external beam (photon and particle) radio-therapy the intensity and/or the range is modulated and the beam is raster scanned over the tumor for delivering the maximum dose to the tumors while minimizing the dose delivered to the surrounding healthy tissue, which is the concept of conformal therapy. Since internal organs, as well as tumors, move with the human body due to respiratory motion, the effectiveness of intensity or range modulated external beam therapy is critically dependent on respiratory motion compensation.

Currently, there are three main types of respiratory motion management devices in use. One, the "Anzai" method, uses a wearable belt with electrical strain sensors that is affixed near the diaphragm of the patient. Shortcomings of this method include the fact that motion is being measured at one plane only, and the device cannot be in the field of view either during an imaging scan or therapy procedure as it distorts the image and the treatment field due to its high attenuating property.

The second class of method use optical techniques (such as Varian RPM, C-Rad and GateCT) using either physical markers or reflectors on the patient from where a light signal is reflected and a motion signal is derived or a structured light is mapped onto the patient. The shortcomings of this method include the fact that the light reflections can be modified significantly by objects in the path including patient clothing or covers that can lead to significant discomfort to the patient, as the patient must remain bare bodied during the procedure in a room that is typically kept colder for managing equipment heating. These methods are harder to implement in imaging than in therapy because most imaging procedures are performed in the bore of the device that does not provide a clear direct line of sight to the patient. In some other cases, a thermal scanner is used to track the breathing motion of the patient and suffers from the same shortcomings as the optically scanning techniques.

The third type uses x-ray sources and detection systems for generating a moving x-ray image of the patient for managing motion during therapy. The shortcomings of this method include the need for significant infrastructure for installation, the requirement of a direct line of sight, and unnecessary added radiation dose to the patient for motion management. In addition, the sensitivity of MRI systems for electromagnetic interference is a key problem for implementing motion management techniques. As such, there are no currently available effective motion management techniques for this very important diagnostic imaging modality.

SUMMARY

Embodiments consistent with principle of the present invention include a method and system of compensating for body deformation during image acquisition. In one embodiment, as image data of a body is acquired, the system acquires peak wavelength data from a plurality of fiber Bragg gratings (FBGs) disposed on the body, with the FBGs aligned along a cartesian coordinate system on the body. Through the FBGs, the system detects effective shifts of the Bragg wavelengths of the FBGs caused by body deformation during image acquisition. The system corrects the acquired image data during image reconstruction to compensate for body deformation during an image scan based on the effective shifts of the Bragg wavelengths of the FBGs aligned along the cartesian coordinate system.

In some embodiments, the system may be used in connection with data acquired through a computed tomography (CT) scan, magnetic resonance imaging (Mill) scan, positron emission tomography (PET) scan, or single photon emission computed tomography (SPECT) scan.

In other embodiments, the system may include moving a body through a cavity of a scanning device and acquiring volumetric image data of a body on a slice by slice basis. The system acquires peak wavelength data from a plurality of fiber Bragg gratings (FBGs) disposed on the body. The system detects effective shifts of the Bragg wavelengths of the FBGs caused by body deformation during image acquisition and controls the movement of the body through the cavity of the scanning device, such that the body does not move and image data is not acquired during body deformation based on the effective shifts of the Bragg wavelengths of the FBGs.

Another embodiment consistent with principles of the invention includes a system for compensating for body deformation during external beam treatment, such as photon beam radiotherapy or proton beam therapy used in connection with the treatment of tumors. In one embodiment, a target region of the body for external beam treatment is identified. The system acquires peak wavelength data from a plurality of fiber Bragg gratings (FBGs) disposed on a body, the FBGs aligned along a cartesian coordinate system. The system directs external beam treatment to the target region. As effective shifts of the Bragg wavelengths of the FBGs caused by body deformation during treatment are detected, the external beam treatment may be redirected to compensate for body deformation during an image scan based on the effective shifts of the Bragg wavelengths of the FBGs aligned along the cartesian coordinate system to maintain focus on the target region.

A garment for real time detection of body deformation during an image scan includes a front portion, made of a compression material and having of plurality of fiber Bragg gratings (FBGs), the front portion disposed on top of a person body, the FBGs aligned along a cartesian coordinate system. The garment includes a plurality of light emitters, each light emitter configured to pulse light waves through a corresponding FBGs and a plurality of light sensors, each light sensor attached to a corresponding FBG and configured to receive pulsed light waves. A processor obtains data through a data acquisition module configured to receive from the light sensors peak wavelengths reflected by the FBG. The processor, which may be embedded in the garment or located remote device or terminal, also includes a comparator configured to determine the effective shifts of Bragg wavelengths due to axial strain on the FBGs. In yet another embodiment, a garment for real time detection of body deformation during an image scan may have FBGs disposed all around a body.

The processor may further include a correction module configured to correct acquired image data to compensate for body deformation during an image scan based on the effective shifts of the Bragg wavelengths of the FBGs aligned along the cartesian coordinate system, or to re-direct an external beam treatment to compensate for body deformation during an image scan based on the effective shifts of the Bragg wavelengths of the FBGs aligned along the cartesian coordinate system to maintain focus on the target region.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Figure 1:
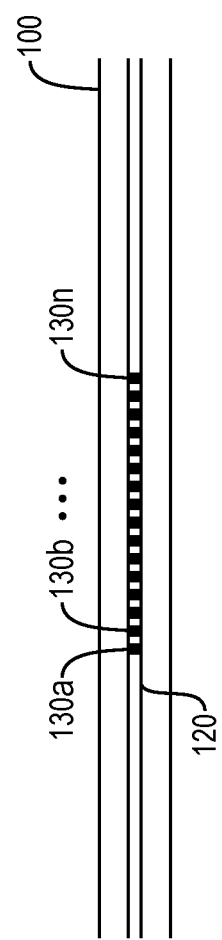
FIG. 1 is a representative FBG in a fiber-core.

As illustrated in FIG. 1, a fiber Bragg grating (FBG) 100 is a small length of optical fiber 120 that comprises a plurality of reflection points 130a-n that create a periodic variation of refractive index. The FBG reflects a unique wavelength ($\lambda B$), centered around a bandwidth, $\Delta\lambda B$. The periodicity $\Lambda$ of the grating is related to the Bragg wavelength $\lambda B$.

$$lB = 2 \cdot n_{eff} \cdot \Lambda \tag{1}$$

$n_{eff}$ is the effective refractive index of the single-mode photosensitive fiber. As the fiber is stretched and grating parameter $\Lambda$ increases by $\delta\Lambda$ while effective refractive index $n_{eff}$ decreases by $\delta n_{eff}$. The Bragg wavelength $\lambda B$ shifts by $$\delta lB = 2\{n_{eff} \cdot \delta\Lambda + \Lambda \cdot \delta n_{eff}\} \tag{1a}$$

By embedding one or more optical fibers with one or more FBG in wearable materials that can be wrapped over parts of anatomically relevant parts of the human body can be used to sense the deformation of that part resulting from physiological processes such as breathing. In certain embodiments consistent with principles of the invention, the deformation data may be used to correct certain distortions caused by the deformation during image acquisition. In other embodiments, the deformation data may be used to assist in the targeted deliverance of certain medical treatments by altering the delivery to compensate for motion induced by respiration. In other embodiments, the time variations of the strain sensing and the distortion may be used to derive a gating signal for physiological processes.

Before one can use the embedded FBG as a strain gauge, the FBG's response function and linearity should be characterized as a function of load. To characterize the FBG's response function and linearity, an electrical strain gauge may be used to calibrate the FBG such that the applied tensile loading approximates readings of the displacement of the body within the Cartesian coordinate system for a three-dimensional object. For the FBG to perform as a reliable strain gauge, the change in the reflection wavelength of the FBG as it gets stretched under tensile load must linearly track the electrical strain gauge data. Once calibrated, the response of an FBG may be reliably used as an embedded strain gauge for detecting object surface deformation. Within reasonable limits on the elasticity of the gauge, it may also be used for detecting the degree to which the object surface has been displaced. Based on a calibration curve comparing pressure against strain or wavelength, along with the strain data from the sensors, one can detect the degree of displacement. In other cases the calibration curves may be derived from comparing reflected Bragg wavelengths to secondary respiratory measurements that can include physical or image based measurements.

Figure 2B:
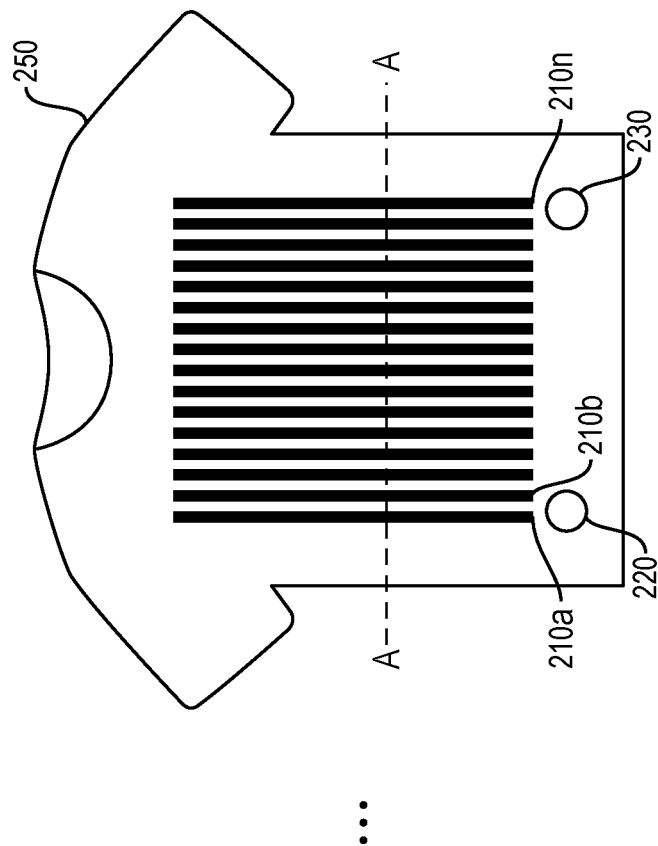
FIGS. 2A and 2B are embodiments of a garment that may be used during an image scan for real time detection of body deformation according to principles of the present invention.
Figure 2A:
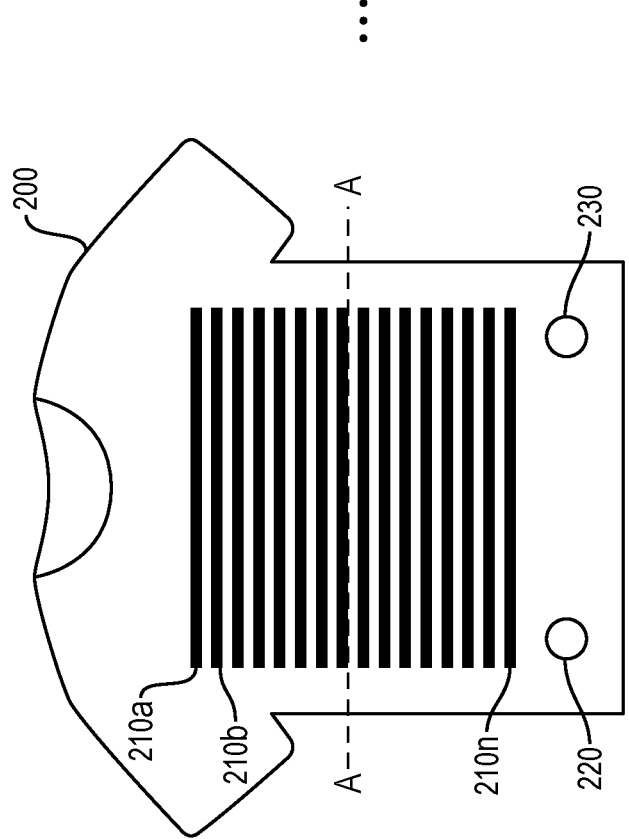

FIGS. 2A and 2B are embodiments of a garment 200 and 250 that may be used during an image scan for real time detection of body deformation according to principles of the present invention. In the garment 200, a plurality of FBG fibers 210a-n are embedded laterally along the garment, running in a direction parallel to a scanning plane A. In the garment 250, a plurality of FBG fibers 210a-n are embedded longitudinally along the garment, running in a direction perpendicular to a scanning plane A. In both embodiments, the garments 200 and 250 may have an input 220 for a laser or light source that is transmitted through the FBG fibers 210a-n. Each FBG 210a-n in connected to a light sensor (not shown) that receives pulsed light waves from the light sources. In addition, the garments 200 and 250 may also include an output 230, where the light sensors may provide data concerning the light transmission through each of the FBGs 210a-n to an external processor that can identify shifts in the effective Bragg wavelengths of the FBGs 210a-n, suggesting deformations in the surface of the object within the garment. In other embodiments, the processor may be internal to the garment, and transmit data via a wireless transmission, such as WiFi or Bluetooth. The multiple FBGs 210a-n can help identify where in the cross-sectional scanning plane there may be specific movement, as each provides a different longitudinal marker along a cartesian coordinate system. Given the low attenuation properties of this garment and that the fiber optic sensors do not create electromagnetic interference, it may be used both while imaging as well as during therapy.

In addition, the change in wavelength measured over time for a free breathing patient wearing such a garment represents the patient specific respiratory signal. The respiratory signal can be used as a gating signal for imaging and therapy in a similar fashion as is used today from respiratory gating devices such as the Anzai belt and the RPM device. The added benefit in this case is that the gating device can be in the imaging or therapy field of view without inducing imaging artifacts or therapy interference.

Figure 3:
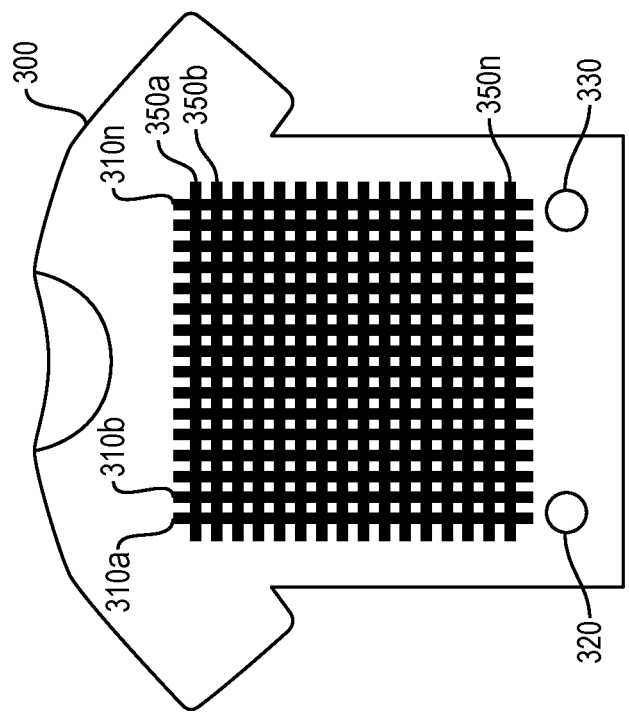
FIG. 3 is second embodiment of a garment that may be used during an image scan for real time detection of body deformation according to principles of the present invention.

FIG. 3 is another embodiment of a garment 300 that may be used during an image scan for real time detection of body deformation according to principles of the present invention. In this garment, a plurality of FBG fibers 310a-n are embedded longitudinally along the garment, and another plurality of FBG fibers 350a-n are embedded latitudinally along the garment. In addition, the garment 300 may also include an output 330, where the light sensors may provide data concerning the light transmission through each of the FBGs 310a-n and FBGs 350a-n to an external processor that can identify shifts in the effective Bragg wavelength of the FBGs 310a-n and FBGs 350a-n, suggesting deformations in the surface of the object within the garment. In other embodiments, the processor may be internal to the garment, and transmit data via a wireless transmission, such as WiFi or Bluetooth. Similar to FBGs 210a-n of garment 200 and 250, the multiple FBGs 310a-n can help identify where in the cross-sectional scanning plane there may be specific movement, as each provides a different longitudinal marker along a cartesian coordinate system. The addition of FBGs 350a-n provide additional data responsive to movements within the object within the garment in a different plane, allowing for more precise information concerning the location and intensity of the movement.

In embodiments of the garment with embedded FBGs for real time measurement of the deformation of the patient body under respiration, one may embed a number of FBGs using a predetermined coordinate system, such as a cartesian coordinate system or polar coordinate system. Additionally, the predetermined coordinate system may be determined in such a way as to balance competing interests of maximizing the fidelity of the measured deformation map while also using the least number of embedded FBGs. This could mean that the embedded FBGs are aligned along a coordinate system with respect to the patient body or in other cases they could be located for a pseudorandom sampling of the patient body. In some embodiments, this could mean that the FBGs could be distributed such that a concentration of embedded FBGs are aligned in a more dense distribution in one region, and loosely distribute in others. Depending on the nature of the garment, the distribution of FBGs within the garment may vary, as a belt or shirt may have a different, more contoured fit around a body than a blanket. Additionally, multiple FBGs can be inscribed inside a single mode optical fiber, and as long as they are separated by an predetermined optimal distance from each other and that each of these FBGs have a unique and distinct Bragg wavelength, a single such optical fiber can be used to measure the strain along its length using a single broadband light source and a single wavelength multiplex detection system. Such a system has distinct advantages over an electrical strain gauge-based system as in the latter case each strain gauge needs is own electrical connection.

By embedding one or more optical fibers with one or more FBGs in wearable materials that can be wrapped over parts of anatomically relevant parts of the human body, the one or more FBGs can be used to sense the motion resulting from physiological processes such as breathing, heart beats, and blood flow, or those resulting from movement of the patient. In certain embodiments consistent with principles of the invention, the motion data may be used to correct certain distortions caused by the motion during image acquisition. In other embodiments, the motion data may be used to assist in the targeted deliverance of certain medical treatments by altering the delivery to compensate for motion induced by respiration, heart beats, blood flow, or patient movements.

In another embodiments detection of such motion can be used to for physiological monitoring of the patient particularly in the case where the patient is under sedation, or the patient is a pediatric patient. The detected motion signals can be used to interrupt the imaging or the therapy procedure for patient safety or other clinical reasons.

Figure 4:
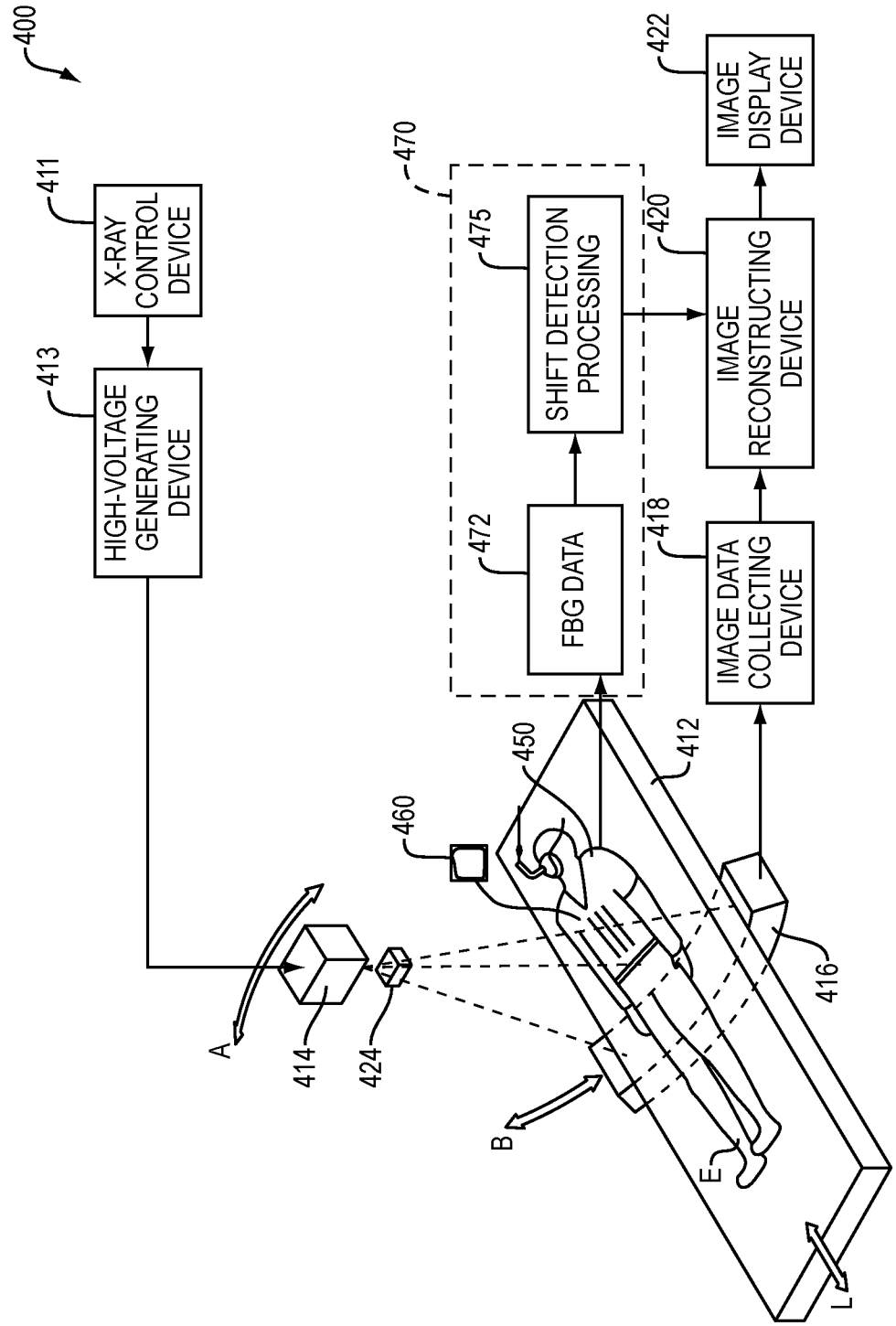
FIG. 4 is an exemplary medical imaging system in which embodiments consistent with the present invention may be used.

FIG. 4. is an exemplary medical imaging system 400 in which embodiments consistent with the present invention may be used. The system 400 may be a computed tomography scanner including an X-ray control device 411, a high-voltage generating device 413 for generating a high voltage according to a shot signal supplied from the X-ray control device 411, a table 412 displaceable in the direction indicated by the arrow L with an examinee E placed thereon, an X-ray source 414 for applying X-rays (photons) to the examinee E according to a high voltage supplied from the high-voltage generating device 13, an X-ray detector 416 for detecting photons that have passed through the examinee E, a data collecting device 418 for collecting examinee-transmitted data based on photons detected by the X-ray detector 416, an image reconstructing device 420 for reconstructing a tomographic image of the examinee E from examinee-transmitted data collected by the data collecting device 418. The X-ray source 414 and the X-ray detector 416 are rotatable in the directions indicated by the arrow A. The components described above make up a CT (Computed Tomography) apparatus. As the X-ray source 414 and the X-ray detector 416 rotate around the examinee E, the image data provides a cross-sectional image scan or "slice." As the examinee moves through the system along the direction L, multiple images "slices" are taken, providing a volumetric scan of the examinee. The system may further include an image display device 422 for displaying a reconstructed tomographic image on a CRT (Cathode Ray tube) or the like.

In typical systems, the CT scanner 400 must not rotate too slowly, and the table 412 must also not pass through too slowly, or respiratory motion during the scan will manifest in body (e.g. abdominal or chest cavity) scans will result in image artifacts in the reconstructed CT volume. With an increase in rotational speed of the scanner 400 and translational speed of the table 412, the intensity of the X-ray source 414 must be higher to acquire adequate data for sufficient image resolution. However, the collision of photons with atoms and molecules of living tissue may cause serious damage to the tissue. The more photons that arrive per second from the X-ray source 414, measured as flux, the greater the potential for tissue damage.

Some embodiments consistent with principles of the present invention include a wearable clothing like device with embedded FBGs for real time detection of respiratory motion. In some embodiments consistent with principles of the invention, that device may be used as a respiratory gating device to concurrently control movement of the CT scanner and dosage of X-rays by separating the acquired data in various stages of the respiratory cycle and the state of the body habitus at that stage, thereby alleviating the need for breath hold or averaging over respiratory cycle. As the device detects respiratory motion, the CT scanner and may pause operation, and resume when the body has returned to its initial respiratory state. Thus, the X-ray dose to the patient may be lowered if the patient can be co-scanned with a respiratory gating device. Similar applications are possible while using this device in a PET or SPECT scan to enable low dose imaging by reducing the injected radiopharmaceutical dose while maintaining diagnostic image quality because of reduced artifacts due to respiratory motion.

In other embodiments, the wearable clothing device may be operated to continuously detect respiratory motion and the degree of deformation resulting from respiratory displacement, such that image data may be acquired without interruption or pausing, with the deformation data used in image reconstruction for deformation correction.

Figure 10:
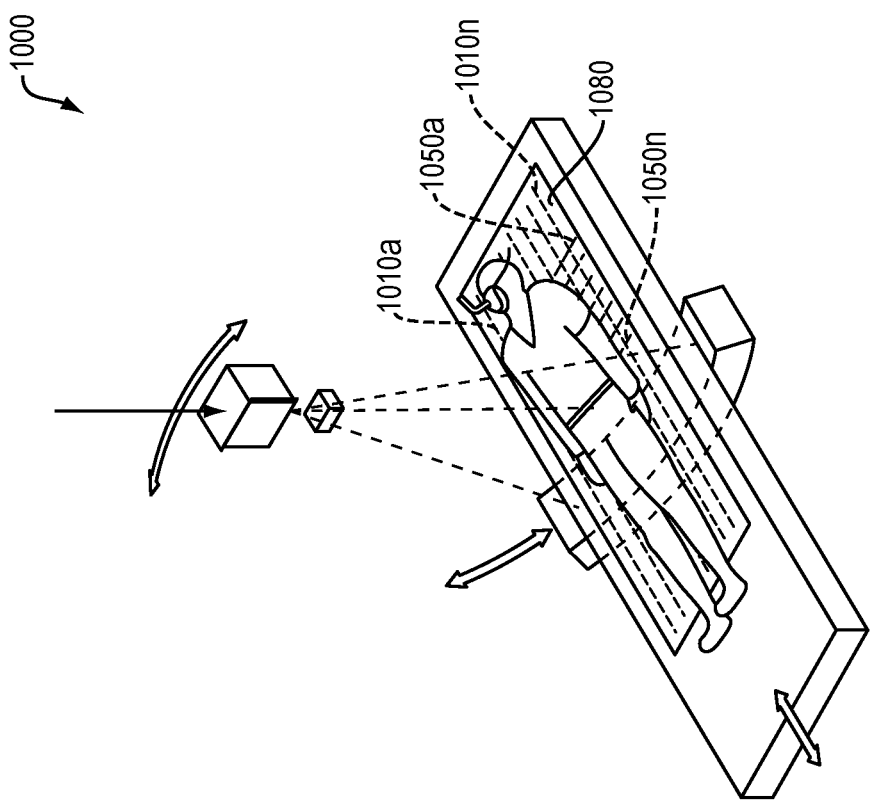
FIG. 10 is an exemplary patient handling system including an embodiment consistent with principles of the invention.

In yet other embodiments, as illustrated in FIG. 10, a patient handling system 1000 may include padding 1080 that has fibers containing the FBGs embedded similar to the garments illustrated in FIGS. 2A, 2B and 3. As shown in FIG. 10, a plurality of FBG fibers 1010$a$-$n$ are embedded longitudinally along the padding 1080, and another plurality of FBG fibers 1050$a$-$n$ are embedded latitudinally along the padding. In alternate embodiments consistent with the teachings herein, the padding 1080 may have FBGs embedded in other configurations to provide data relating to movement or displacement of a body on the padding. Such fibers can also be embedded directly in the patient handling systems (patient beds) of medical imaging and radiation therapy devices. As with the garments shown in FIGS. 2A, 2B and 3, the padding may include an output (not shown), where light sensors may provide data to an external processor. The FBGs may be used to obtain both the deflection of the bed under a patient specific loading as well as a respiratory signal from the patient in contact with the bed. Both of these parameters may be used for optimizing the image acquisition of the patient and for the therapy delivery to the patient.

Figure 5B:
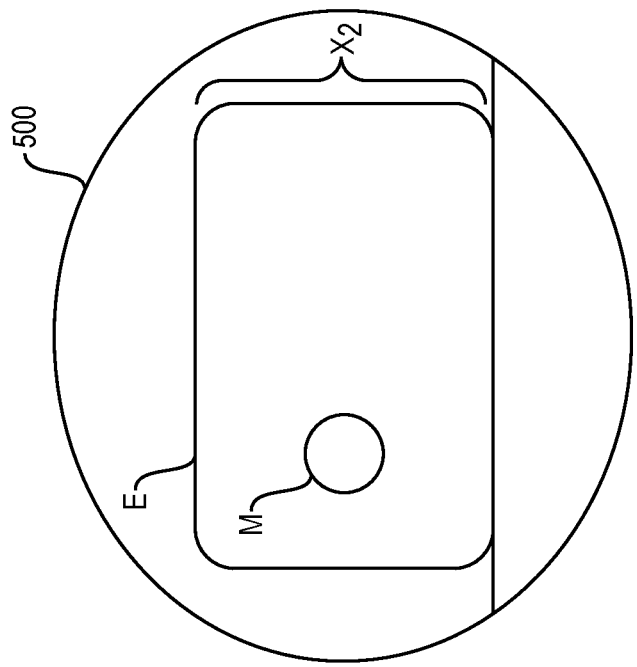
FIGS. 5A and 5B are cross sectional images that may be acquired by a medical imaging system.
Figure 5A:
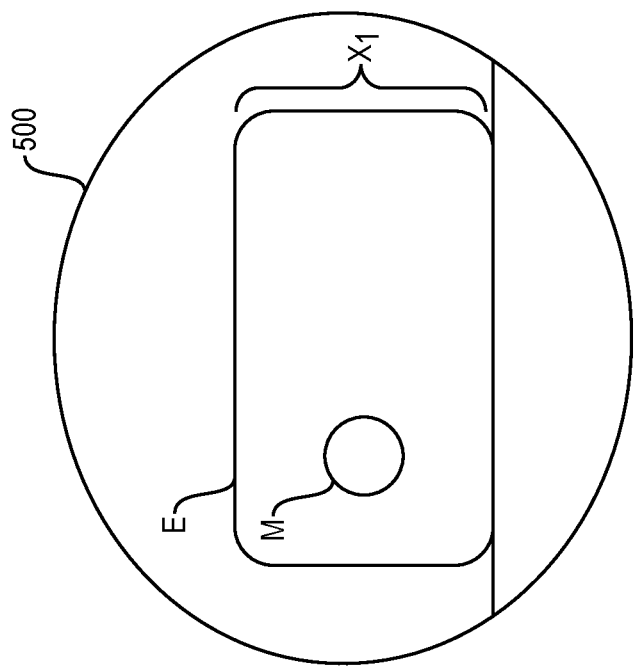

FIG. 5A is a cross sectional image 500A of an examinee E that may be acquired by a medical imaging system. FIG. 5B shows a cross sectional image 500B of the examinee E affected by respiratory motion (e.g. an expansion of the body cavity during inhalation). As a scanner, such as the CT scanner 400 in FIG. 4, takes multiple image slices, the deformation may create deformations in the volumetric scan. In the image 500A of FIG. 5A, the height of the cross section of examinee E's body is $X_1$. In the image 500B of FIG. 5B, because of inhalation, the height of the cross section of examinee E's body is slightly higher to $X_2$. Because the CT scanner 400 is taking multiple slices along the examinee E along direction L, sudden movement between slices (e.g. 500A and 500B) creates a significant variance that results in a distorted volumetric image within the cartesian plane. In both cross sectional images 500A and 500B, a mass M may be located within the scan, and its relative position within the volumetric scan may be detected.

Referring back to FIG. 4, the examinee E may be wearing a garment 450 consistent with principles of the present invention. Such garment 450 may be in communication with a light emitter 460 that transmits light through FBGs (not shown in FIG. 4) embedded within the garment 450. As the examinee E pass through the scanner 400 along direction L, a processor 470 including a data acquisition module 472 receives data from the light sensors (not shown in FIG. 4) attached to the FBGs. A comparator 475 in the processor 470 can identify the effective shifts in the refractive index of the FBGs, due to axial strain on the FBGs and suggest deformations in the surface of the object within the garment. As those deformations are detected, the processor 470 may send deformation correction information to the image reconstruction module 420 to allow for image compensation for any movement. In other embodiments, the processor 470, including the FBG data acquisition module 472 and comparator 475, may be included in the same apparatus as the data collection device 418 and image reconstruction device 420.

Figure 6:
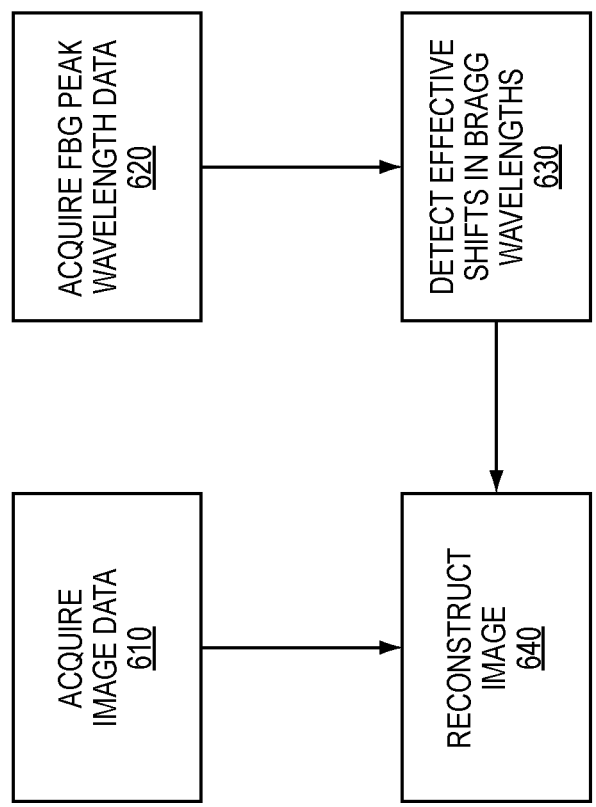
FIG. 6 is a flowchart illustrating a method of compensating for body deformation during image acquisition.

FIG. 6 is a flowchart illustrating a method of compensating for body deformation during image acquisition of an examinee. As the image data of the examinee is acquired at step 610, peak wavelength data in acquired at step 620 from a plurality of fiber Bragg gratings (FBGs) disposed on the body of the examinee. Effective shifts of the Bragg wavelengths of the FBGs caused by body deformation during image acquisition are detected at step 630. If shifts are detected, the acquired image data is corrected at step 640 during image reconstruction in order to compensate for body deformation during the image scan based on the effective shifts of the Bragg wavelengths of the FBGs aligned along the cartesian coordinate system.

In other embodiments consistent with principles of the present invention, a wearable clothing like device with embedded FBGs for real time detection of respiratory motion may be used to detect body motion (e.g. motion induced by respiration, or muscle spasms) in order to assist with targeted delivery of therapy, such as external beam radiotherapy. By detecting body motion, the therapy may adjust positioning and deliver the maximum dose to a tumor and the minimum dose to the surrounding healthy tissue.

Figure 7:
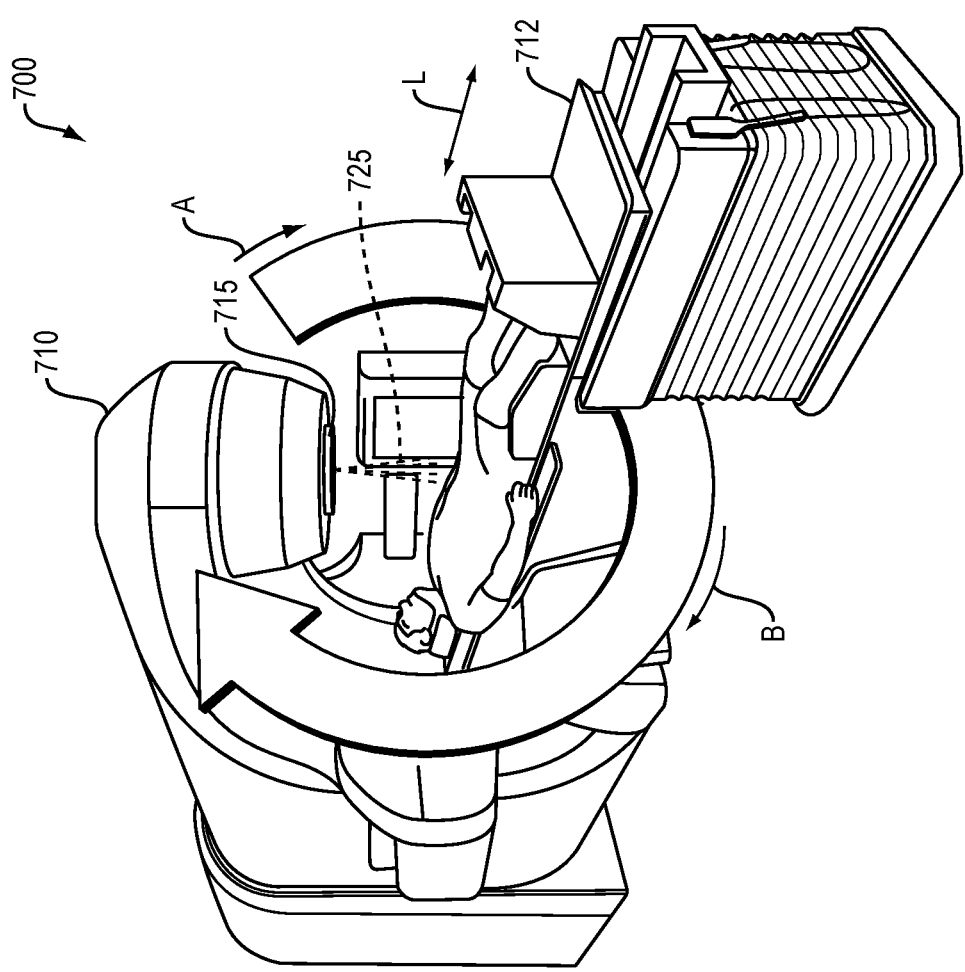
FIG. 7 is an exemplary medical device for external beam treatment in which embodiments consistent with the present invention may be used.

FIG. 7 is an exemplary medical device 700 for external beam treatment in which embodiments consistent with the present invention may be used. A medical linear accelerator (LINAC) is a commonly used devices for external beam radiation treatments for patients with cancer. A linear accelerator includes a gantry 710 that typically uses high Radio-Frequency (RF) electromagnet waves to accelerate charged particles (i.e. electrons) to high energies in a linear path, inside a tube like structure called the accelerator waveguide (not shown in FIG. 7). In alternate embodiments, the medical device may include multiple emitters. An emitter 715 emits high energy x-rays 725 from the machine, directed to the patient's tumor. The patient lies on a moveable treatment table 712. The patient is positioned, and such position may be monitored using lasers or mechanical means (not shown in FIG. 7). The treatment table moves in and out of the gantry in direction L. In some alternative medical devices, the table may also move the patient from left to right (perpendicular to direction L) and/or up and down (closer or further from the emitter 715). The gantry may be rotated around the patient, and radiation treatment may be delivered to a tumor within a patient from many angles by rotating the gantry and moving the treatment couch.

Figure 8:
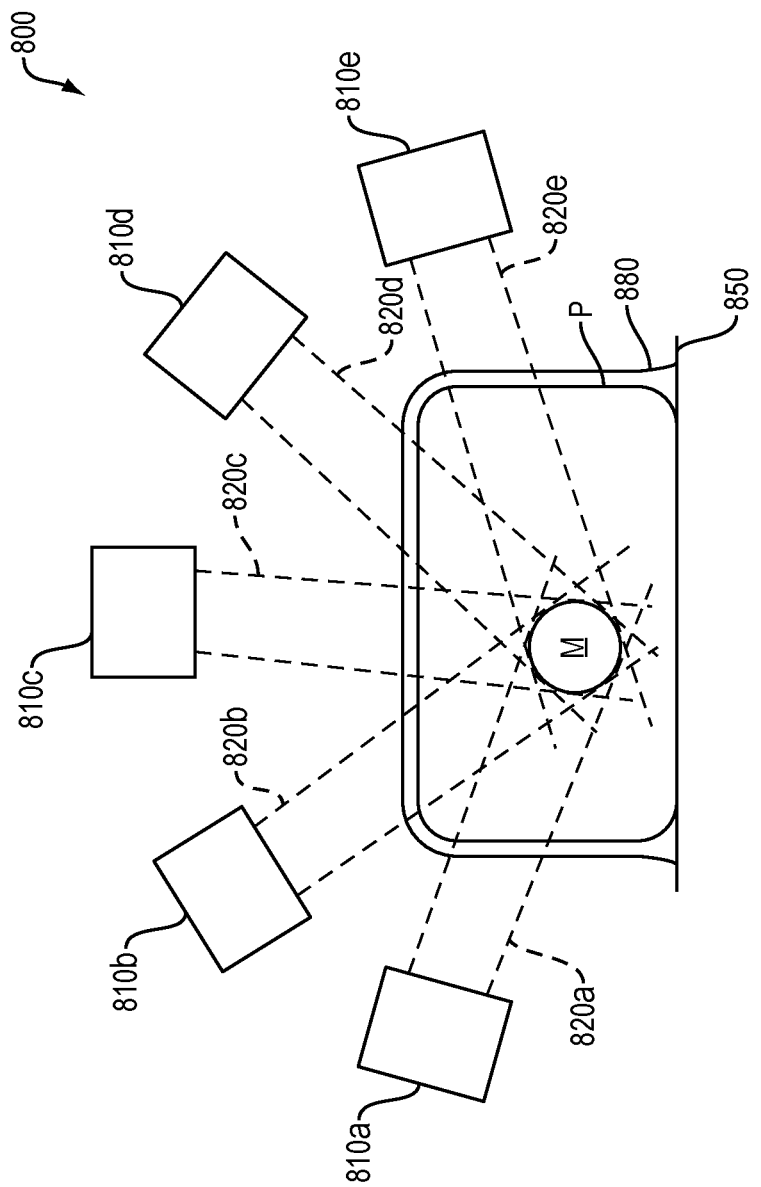
FIG. 8 is a cross sectional view of a body illustrating external beam treatment by the medical device FIG. 7.

FIG. 8 is a cross sectional view 800 of a patient P illustrating external beam treatment by the medical device FIG. 7. The illustration shows an emitter at various positions 810$a$-$e$ as it rotates around the patient P. At the first position 810$a$, the emitter 810 directs some form of beam treatment, such radiation therapy, through the patient at the mass M. As the gantry rotates through a second position 810$b$, the beam continues to pass through the patient from a different angle, but continues to target mass M. The radiation treatment passes through healthy tissue, but because the emitter continues to rotate, the exposure to the radiation in the health tissue is minimized. Consistent with principles of the invention, the patient P may wear a garment 880 that includes FBGs (not shown in FIG. 8) embedded within the garment. As discussed above with respect to FIG. 2 and FIG. 3, such garment 880 may be in communication with a light emitter (not shown in FIG. 8) that transmits light through the FBGs embedded within the garment 880. As the patient P passes through the medical device and receives treatment, a processor similar to the described in connection with FIG. 4, including a data acquisition module receives data from the light sensors attached to the FBGs. Effective shifts in the refractive index of the FBGs, due to axial strain on the FBGs suggest deformations in the surface of the object within the garment, allowing the medical device to shift the positioning of the patient or the emitters in order to better target the mass M and minimize dosage to non-targeted tissues.

By using simultaneously acquired anatomic or functional imaging data along with motion and deformation data on patients wearing a garment embedded with one or more FBGs, one can estimate the motion of internal organs and tumors by employing machine learning algorithms, such as a regression or decision tree algorithm. The image data may be correlated with the motion and deformation data such that the better track objects, such as internal organs or tumors, within the scanned images. As more image data is obtained, displacement estimations based on detected motion may be further refined. These machine learning techniques can be used during imaging and therapy procedures conducted with the embedded FBG patient motion/body deformation sensing garments for improving diagnostic image quality and radiation therapy treatment efficacy.

Figure 9:
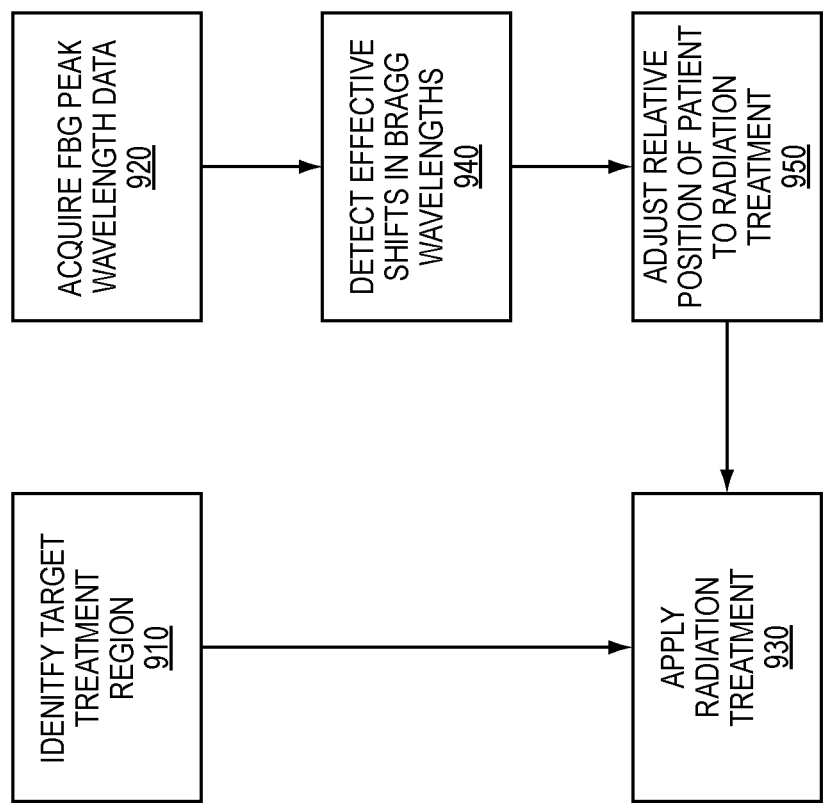
FIG. 9 is a flowchart illustrating a method of compensating for body deformation during external beam treatment.

FIG. 9 is a flowchart illustrating a method of compensating for body deformation during external beam treatment. As the medical device identifies a target region of a body for external beam treatment in step 910, peak wavelength data is acquired at step 920 from a plurality of fiber Bragg gratings (FBGs) disposed on the body of the examinee. External beam treatment is directed to the target region in step 930. Effective shifts of the Bragg wavelengths of the FBGs caused by body deformation during treatment are detected at step 940. In step 950, upon detecting any shifts, external beam treatment may be shifted to compensate for body deformation during an image scan based on the effective shifts of the Bragg wavelengths of the FBGs aligned along the cartesian coordinate system to maintain focus on the target region. In some embodiments, re-directing the external beam treatment may include not applying the treatment to the body by withholding the application of radiation. The relative position of the patient to the radiation treatment may be adjusted by either moving the position of the emitter in the gantry or the treatment table.

The low attenuation properties of a garment with embedded FBGs allows it to provide more accurate medical imaging and radiotherapy with little to no interference. In addition, it may also increase patient comfort and reduce radiation dose. Such a device will also open the possibility to make a new class of low cost scanners as the imaging is done as a function of body deformation and can make such imaging modalities more widely accessible even to the most cost sensitive population groups.

While example embodiments have been particularly shown and described, it will be understood by those skilled in the art that various changes in form and details may be made therein without departing from the scope encompassed by the appended claims.

It should be understood that the example embodiments described above may be implemented in many different ways. In some instances, the various methods and machines described herein may each be implemented by a physical, virtual or hybrid general purpose computer having a central processor, memory, disk or other mass storage, communication interface(s), input/output (I/O) device(s), and other peripherals. The general purpose computer is transformed into the machines that execute the methods described above, for example, by loading software instructions into a data processor, and then causing execution of the instructions to carry out the functions described, herein.

As is known in the art, such a computer may contain a system bus, where a bus is a set of hardware lines used for data transfer among the components of a computer or processing system. The bus or busses are essentially shared conduit(s) that connect different elements of the computer system, e.g., processor, disk storage, memory, input/output ports, network ports, etcetera, which enables the transfer of information between the elements. One or more central processor units are attached to the system bus and provide for the execution of computer instructions. Also attached to system bus are typically I/O device interfaces for connecting various input and output devices, e.g., keyboard, mouse, displays, printers, speakers, etcetera, to the computer. Network interface(s) allow the computer to connect to various other devices attached to a network. Memory provides volatile storage for computer software instructions and data used to implement an embodiment. Disk or other mass storage provides non-volatile storage for computer software instructions and data used to implement, for example, the various procedures described herein.

Embodiments may therefore typically be implemented in hardware, firmware, software, or any combination thereof.

In certain embodiments, the procedures, devices, and processes described herein constitute a computer program product, including a non-transitory computer-readable medium, e.g., a removable storage medium such as one or more DVD-ROM's, CD-ROM's, diskettes, tapes, etcetera, that provides at least a portion of the software instructions for the system. Such a computer program product can be installed by any suitable software installation procedure, as is well known in the art. In another embodiment, at least a portion of the software instructions may also be downloaded over a cable, communication and/or wireless connection.

Further, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etcetera.

It also should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and, thus, the data processors described herein are intended for purposes of illustration only and not as a limitation of the embodiments.

While this invention has been particularly shown and described with references to example embodiments thereof, it will be understood by those skilled in the art that various changes in form and details may be made therein without departing from the scope of the invention encompassed by the appended claims.

What is claimed is:

1. A method of compensating for body deformation during image acquisition, the method comprising:
   acquiring image data of a body;
   acquiring peak wavelength data from a plurality of fiber Bragg gratings (FBGs) disposed on the body, the FBGs aligned along a predetermined coordinate system;
   detecting effective shifts of the Bragg wavelengths of the FBGs caused by body deformation during image acquisition; and
   controlling the movement of the body through a cavity in a scanning device and controlling the acquisition of the image data during body deformation based on the effective shifts of the Bragg wavelengths of the FBGs.

2. The method of claim 1 wherein the image data is acquired from a computed tomography (CT) scan, magnetic resonance imaging (MM) scan, positron emission tomography (PET) scan, or single photon emission computed tomography (SPECT) scan.

3. The method of claim 1 wherein the predetermined coordinate system is a cartesian coordinate system.

4. The method of claim 3 wherein the effective shifts of the Bragg wavelengths measure strain along dual-axis.

5. The method of claim 1 further comprising:
   identifying an object within the body;
   and estimating movement of the object by correlating the acquired image data with the effective shifts of the Bragg wavelengths due to motion and deformation to estimate the motion of the object within the body.

6. The method of claim 5 further comprising applying machine learning algorithms to improve estimating movement of the object.

7. The method of claim 5 wherein the object is an internal organ or a tumor.

8. The method of claim 1 further comprising reconstructing the image data and correcting the acquired image based on effective shifts in order to compensate for body deformation during the image scan.

9. A method of compensating for body deformation during image acquisition, the method comprising:
   moving a body through a cavity of a scanning device;
   acquiring image data of a body;
   acquiring peak wavelength data from a plurality of fiber Bragg gratings (FBGs) disposed on the body;
   detecting effective shifts of the Bragg wavelengths of the FBGs caused by body deformation during image acquisition;
   generating a respiratory gating signal based on effective shifts of the Bragg wavelength measured over time; and
   controlling the movement of the body relative to the cavity of the scanning device based on the respiratory gating signal, such that the body does not move and image data is not acquired during body deformation based on the effective shifts of the Bragg wavelengths of the FBGs.

10. The method of claim 9 wherein the image data is acquired from a computed tomography (CT) scan, magnetic resonance imaging (MM) scan, positron emission tomography (PET) scan, or single photon emission computed tomography (SPECT) scan.

11. The method of claim 9 wherein the predetermined coordinate system is a cartesian coordinate system.

12. The method of claim 11 wherein the effective shifts of the Bragg wavelengths measure strain along dual-axis.

13. The method of claim 9 further comprising:
   identifying an object within the body;
   and estimating movement of the object by correlating the acquired image data with the effective shifts of the Bragg wavelengths due to motion and deformation to estimate the motion of the object within the body.

14. The method of claim 13 further comprising applying machine learning algorithms to improve estimating movement of the object.

15. The method of claim 13 wherein the object is an internal organ or a tumor.

16. The method of claim 9 further comprising reconstructing the image data and correcting the acquired image based on effective shifts in order to compensate for body deformation during the image scan.

17. A method of compensating for body deformation during external beam treatment, the method comprising:
   identifying a target region of the body for external beam treatment;
   acquiring peak wavelength data from a plurality of fiber Bragg gratings (FBGs) disposed on a body, the FBGs aligned along a cartesian coordinate system;
   directing external beam treatment to the target region;
   detecting effective shifts of the Bragg wavelengths of the FBGs caused by body deformation during treatment; and
   re-directing the external beam treatment to compensate for body deformation during an image scan based on the effective shifts of the Bragg wavelengths of the FBGs aligned along the cartesian coordinate system to maintain focus on the target region.

18. The method of claim 17 wherein the external beam treatment is external beam radiotherapy or proton beam therapy.

19. The method of claim 17 wherein re-directing the external beam treatment includes not applying the treatment to the body.

20. The method of claim 17 wherein the predetermined coordinate system is a cartesian coordinate system.

21. The method of claim 20 wherein the effective shifts of the Bragg wavelengths measure strain along dual-axis.

22. The method of claim 17 wherein the target region includes an object within the body and further comprising estimating the movement of the object in the body by correlating the acquired image data with the effective shifts of the Bragg wavelengths over motion and deformation.

23. The method of claim 22 further comprising applying machine learning algorithms to improve estimating the movement of the object.

24. The method of claim 22 wherein the object is a tumor.

* * * * *

UNITED STATES PATENT AND TRADEMARK OFFICE
CERTIFICATE OF CORRECTION

PATENT NO. : 12,044,556 B2
APPLICATION NO. : 17/224855
DATED : July 23, 2024
INVENTOR(S) : Manojeet Bhattacharya It is certified that error appears in the above-identified patent and that said Letters Patent is hereby corrected as shown below:

In the Specification

Column 1, Line 22, delete "magnetic resonance imaging (MM), and positron" and insert -- magnetic resonance imaging (MRI), and positron --

Column 2, Line 31, delete "magnetic resonance imaging (Mill) scan" and insert -- magnetic resonance imaging (MRI) scan --

In the Claims

Column 11, Line 20, Claim 2, delete "magnetic resonance imaging (MM) scan" and insert -- magnetic resonance imaging (MRI) scan --

Column 12, Line 1, Claim 10, delete "resonance imaging (MM) scan" and insert -- resonance imaging (MRI) scan --

Signed and Sealed this
First Day of October, 2024

Katherine Kelly Vidal
*Director of the United States Patent and Trademark Office*